(12) United States Patent
Benkewitz

(10) Patent No.: US 8,687,873 B2
(45) Date of Patent: Apr. 1, 2014

(54) INSPECTION METHOD

(75) Inventor: Markus Benkewitz, Dresden (DE)

(73) Assignee: HSEB Dresden GmbH, Dresden (DE)

( * ) Notice: Subject to any disclaimer, the term of this patent is extended or adjusted under 35 U.S.C. 154(b) by 52 days.

(21) Appl. No.: 13/289,261

(22) Filed: Nov. 4, 2011

(65) Prior Publication Data

US 2012/0051623 A1 Mar. 1, 2012

(30) Foreign Application Priority Data

Nov. 5, 2010 (DE) .................. 10 2010 060 376

(51) Int. Cl.
*G06K 9/00* (2006.01)
(52) U.S. Cl.
USPC .......................................................... 382/149
(58) Field of Classification Search
None
See application file for complete search history.

(56) References Cited

U.S. PATENT DOCUMENTS

| 4,692,943 A | 9/1987 | Pietzsch et al. |
| 6,832,007 B1 * | 12/2004 | Zhang et al. .................. 382/257 |
| 2008/0107328 A1 * | 5/2008 | Chen et al. ..................... 382/149 |

OTHER PUBLICATIONS

Shankar et al.; Classification of Defects on Semiconductor Wagers using Priority Rules; Defects and Diffusion Forums; 2004; pp. 135-148; vol. 230-232.
Tee et al.; Defect Cluster Segmentation for CMOS Fabricated Wafers; 2009 Conference on Innovative Technologies in Intelligent Systems and Industrial Applications (CITISIA 2009); Monash University, Sunway Campus, Malaysia; Jul. 25 and 26, 2009.

* cited by examiner

*Primary Examiner* — Stephen R Koziol
*Assistant Examiner* — Raphael Schwartz
(74) *Attorney, Agent, or Firm* — Thorpe North & Western LLP

(57) ABSTRACT

A method for inspecting flat objects, especially wafers, comprising the steps of scanning a digital image of the object surface; detecting defects on the object surface; generating a binary image of the scanned image where only detected defects are represented; and compressing the binary image; and wherein detected defects are enlarged before compressing by adding additional, adjacent image points to the image points of the defects. It may be advantageous if only defects having a selected size, shape or position are enlarged.

12 Claims, 3 Drawing Sheets

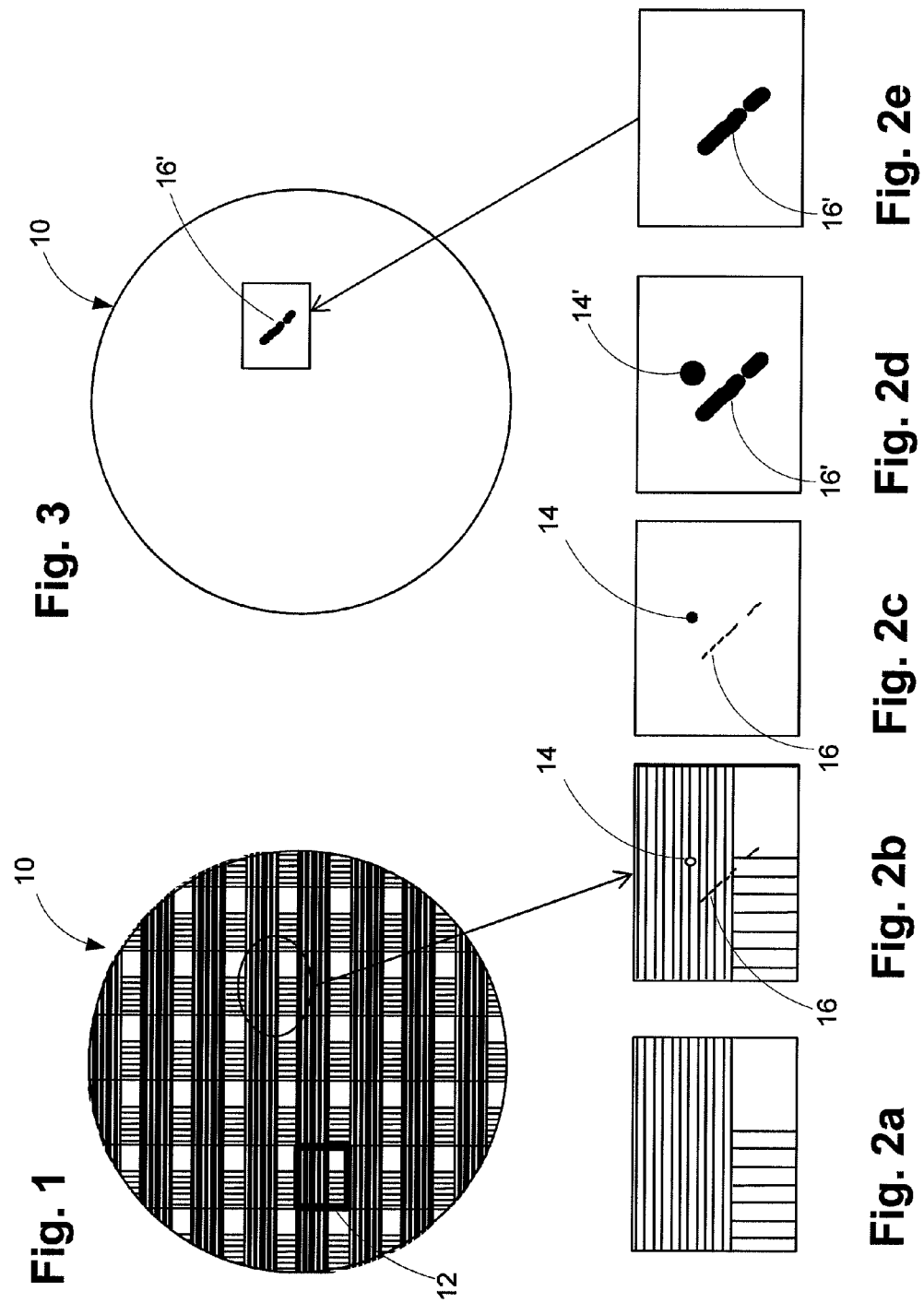

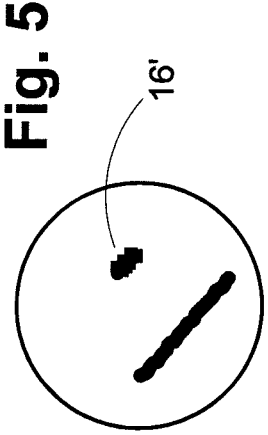
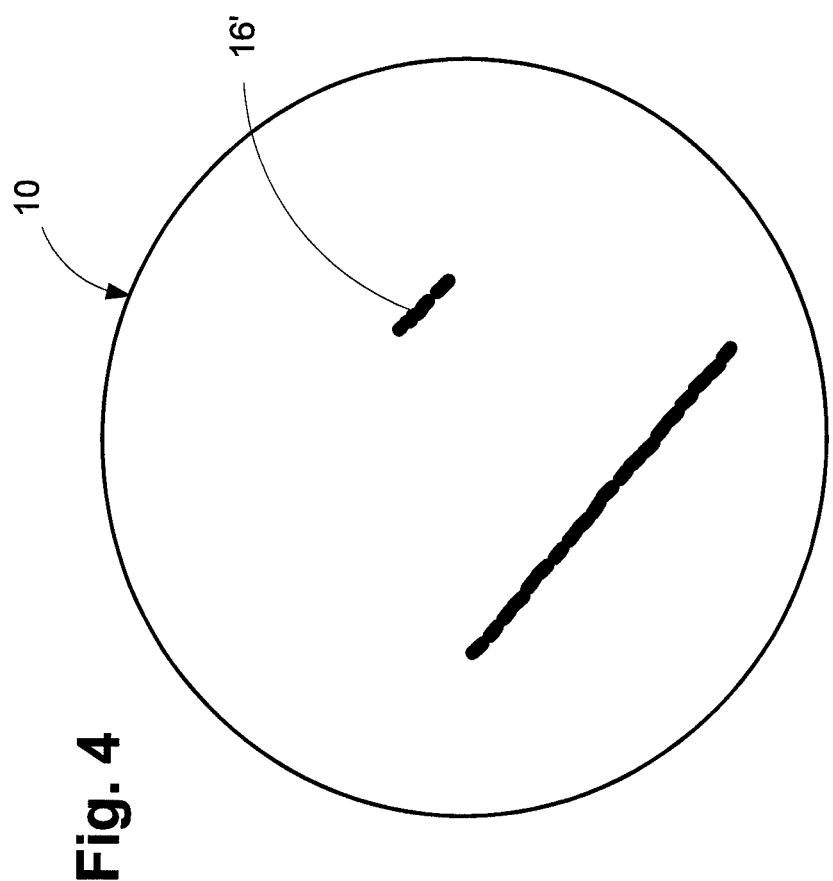

INSPECTION METHOD

TECHNICAL FIELD

The invention relates to a method for inspecting flat objects, especially wafers, comprising the steps of:
(a) taking an image of the object surface;
(b) detecting defects on the object surface.

In different branches of the industry flat products are inspected for defects with imaging methods. In semiconductor- and solar cell industry these products are, amongst others, wafers. Wafers are discs of semiconductor-, glass-, sheet- or ceramic materials. The wafers are inspected entirely or at least with large portions thereof. Such an inspection is called Macro-inspection. The lateral resolution required for the detection of the interesting defects increases with developments of the general production technique. Typically, resolutions of 5 microns or less in macro-inspection are required for new technologies. At the same time, devices having a high throughput of wafers for inspection are desirable.

Analogue tasks must be solved in different branches of the industry. Displays must be inspected for defects during their production in flat-panel industry. Imaging methods for the entire surface of the displays are used for the search of defects. In the electro industry defects on series of objects are determined with optical methods during the inspection of circuit boards.

It is a need common for all such applications to have a quick inspection for a high amount of objects which are usually of the same kind. Such objects are circuit boards, wafers, solar cells, displays and the like. All applications also use sensors for the generation of a large image of the objects. The images can be generated with optical imaging systems or with point-wise operating systems, depending on the kind of the defects searched for. Optical imaging systems are, for example, array- or line cameras. Point-wise operating sensors are, for example, detectors for measuring the reflection of optical rays, microwaves or acoustic waves. Also, magnetic sensors may be used.

PRIOR ART

It is known to scan wafers or other surfaces and to compare the image with a defect-free or almost defect-free reference image at first. A new image can be generated from the differences between the scanned image and the reference image. Such an image may also be generated in the form of a binary image. This means: Either there is a defect on a particular image point or there is no defect. Defects on the surface, such as scratches, dirt or production caused defects are very well visible in the form of black defects on a white background. Defects may be very small and have a size in the order of magnitude of only one image point in the range of 5 microns.

Real images of the object surface are composed of a plurality of individual images. They require much storage capacity in the range of Gbytes. Thereby handling of the images is difficult. It is, therefore, common to compress the images with an ordinary algorithm. The required storage space is then in the range of only a few Mbytes. Information is lost upon compressing. Very small defects are not shown at all anymore in the compressed image.

The term "KLARF" (KLA Result file) is known to describe a text file storing data relating to the defects on a surface as some kind of defect map. This data format is widely used, especially in the semiconductor industry, as the common transmission way for defect information. The data comprised in the file include the positions of the defects and information about their size. If the text file is translated back and the defects are inserted into a map, each defect is represented by a simple point. Information relating to the shape of the defect is lost. In practically occurring surfaces there are often very many defects which are unimportant. Such defects are also represented by a simple point. The observer cannot identify important defects in the mass of various defects.

DISCLOSURE OF THE INVENTION

It is an object of the invention to provide a method of the above mentioned kind with small need of storage capacity with low information losses by compression. According to an aspect of the invention, this object is achieved with a method which is characterized in that detected defects are enlarged before compressing by adding additional, adjacent image points to the image points of the defects.

It is advantageous if only defects having a selected size, shape or position are enlarged. In particular, defects may be detected by comparing the scanned image with a reference image.

The present invention is based on the finding that the information content can be essentially maintained if the defects are enlarged first. Further image points are attributed to each image point which has been recognized as being part of a defect. A defect having the size in the order of magnitude of only one image point is then stored, for example, in the form of this image point and additionally with the surrounding 8 image points. A circular shaped or line shaped defect will then have a thicker "line width", the shape and the diameter of the circle or the line, however, will be maintained as information.

Suitable criteria may be set for enlarging only selected defects. This may be, for example, a minimum size and a maximum size.

The storage requirements and the requirements for the transmission capacity can be further reduced if the image is stored and/or transmitted in portions, where only such portions are selected where defects have been detected and/or which are important for the further processing of the surface.

Further modifications of the invention are subject matter of the subclaims. An embodiment is described below in greater detail with reference to the accompanying drawings.

BRIEF DESCRIPTION OF THE DRAWINGS

FIG. 1 is a schematic representation of a scanned image of a wafer with a structured surface.

FIG. 2a shows a reference structure element.

FIG. 2b shows a detail of FIG. 1 in an enlarged representation with a structure element and defects.

FIG. 2c shows a difference image which was obtained from FIG. 2b and the reference structure element of FIG. 2a.

FIG. 2d shows the difference image of FIG. 2c with enlarged defects.

FIG. 2e shows the difference image with enlarged defects of FIG. 2d after filtering.

FIG. 3 shows the defect of FIG. 2e and its position on the wafer.

FIG. 4 shows all defects of the wafer without repeating structures.

FIG. 5 is a small overview image of the wafer.

DESCRIPTION OF THE EMBODIMENT

Figure 6B:
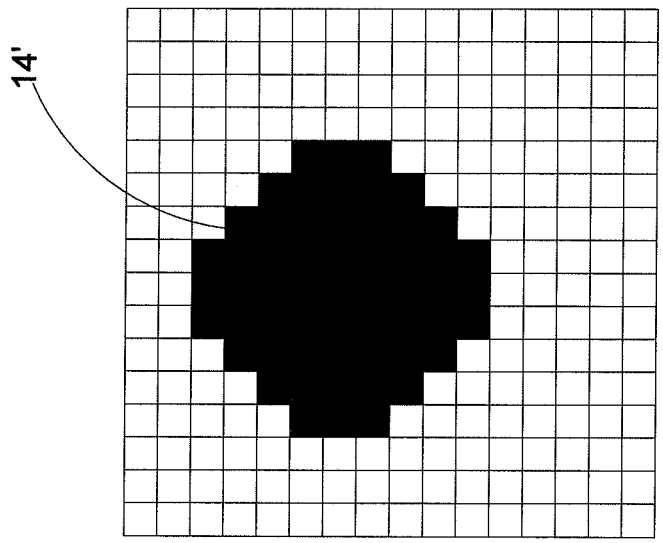
FIGS. 6a-b illustrate the enlargement of defects.

FIG. 1 is a schematic representation of a scanned image of a wafer 10. The wafer 10 has a structured surface with repeating structure elements (dies). An example of such a structure element 12 is shown with bold lines in the representation for a better overview.

FIG. 2a shows such a structure element in an enlarged view. The structure element has no defects and is, therefore, used as a reference. In practice, such references may be taken from the same wafer image. However, there are numerous wafers for inspection where there is the possibility to obtain the reference from a defect-free or almost defect-free reference wafer, also. The methods of how to obtain reference images of individual structure elements, portions or entire wafers are generally well known and, therefore, need not be described here in further detail.

FIG. 2b shows a detailed structure element of the wafer with defects shown in FIG. 1. The defects in FIG. 1 cannot be seen with mere eye sight. The enlargement of FIG. 2b, however, shows that there are a very small defect 14 in the form of a circle and a slightly larger defect 16 in the form of an interrupted line.

Comparison of the scanned image of FIG. 2b and the reference image in FIG. 2a will provide a difference image. The difference image is shown in FIG. 2c. Defects 14 and 16 can still be seen, but not the structures there behind.

The wafer image composed of a plurality of images of the structure elements as shown in FIG. 2 requires much storage capacity and transmission capacity. Therefore, it is normally compressed. With the compression of a representation such as, for example, the one in FIG. 2c, information about small defects 14 and 16 is lost. The defects are, therefore, enlarged before compression.

Figure 6A:
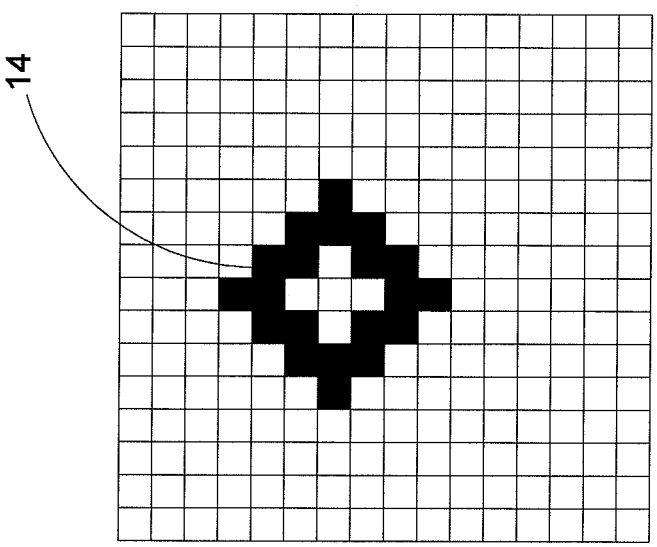

An example of such an enlargement of defect 14 is illustrated in FIG. 6. The defect 14 is distributed on image points in a circular arrangement, as they are shown in FIG. 6a. The other image points are white. Further image points are then attributed to each of the image points, which are also black, i.e. the value is digitally defined as "defect". In the present example the eight directly adjacent image points are attributed to each image point. Each defect image point is, therefore, represented by nine image points. Thereby, the shape of the circle changes to a single spot 14'. The diameter, however, is maintained apart from the larger "line width". This is shown in FIG. 6b. FIG. 2d shows the difference image of FIG. 2c with enlarged defects. It is understood that any factor can be applied for the enlargement and is not limited to this scale.

Often only defects having a selected size, shape or position are important for the inspection of wafers. These can be maintained according to a suitable filter mechanism. FIG. 2e shows the difference image of the example with enlarged defects according to FIG. 2d after filtering. The circle 14 was filtered while the line 16 is maintained in the enlarged form 16'.

FIG. 3 shows the defect 16' of FIG. 2e with its position on the wafer 10. The enlargement method described above can be repeated for all defects. This will provide an image, as it is shown, by way of example, in FIG. 4. The shape and the position of the defects can be well seen as opposed to the representation in FIG. 1. Depending on how this image shall be used, it is often sufficient to store an overview image. An example is shown in FIG. 5. The defects can be well seen in such an overview image, also.

What is claimed is:

1. A method for inspecting flat objects, especially wafers, having an object surface, the method comprising the steps of:
   (a) scanning a digital image of said object surface;
   (b) detecting defects on said object surface;
   (c) generating a binary image of said scanned digital image where only detected defects are represented; and
   (d) compressing said binary image; wherein
   (e) detected defects are enlarged before compressing by adding additional, adjacent image points to said image points of said defects.

2. A method according to claim 1, and wherein only defects having a selected size, shape or position are enlarged.

3. A method according to claim 2, and wherein defects are detected by comparing said scanned digital image with a digital reference image.

4. A method according to claim 3, and wherein said scanned digital image is stored or transmitted in portions, where only such portions are selected where defects have been detected and which are important for further processing of said object surface.

5. A method according to claim 2, and wherein said scanned digital image is stored or transmitted in portions, where only such portions are selected where defects have been detected and which are important for further processing of said object surface.

6. A method according to claim 1, and wherein defects are detected by comparing said scanned digital image with a digital reference image.

7. A method according to claim 6, and wherein said scanned digital image is stored or transmitted in portions, where only such portions are selected where defects have been detected and which are important for further processing of said object surface.

8. A method according to claim 1, and wherein said scanned digital image is stored or transmitted in portions, where only such portions are selected where defects have been detected and which are important for further processing of said object surface.

9. A method according to claim 6, and wherein said scanned digital image is stored and transmitted in portions, where only such portions are selected where defects have been detected and which are important for further processing of said object surface.

10. A method according to claim 3, and wherein said scanned digital image is stored and transmitted in portions, where only such portions are selected where defects have been detected and which are important for further processing of said object surface.

11. A method according to claim 2, and wherein said scanned digital image is stored and transmitted in portions, where only such portions are selected where defects have been detected and which are important for further processing of said object surface.

12. A method according to claim 1, and wherein said scanned digital image is stored and transmitted in portions, where only such portions are selected where defects have been detected and which are important for further processing of said object surface.

* * * * *